US009924928B2

(12) United States Patent
Choi et al.

(10) Patent No.: US 9,924,928 B2
(45) Date of Patent: Mar. 27, 2018

(54) ULTRASONIC DIAGNOSTIC APPARATUS, ULTRASONIC IMAGE PROCESSING APPARATUS, AND MEDICAL IMAGE DIAGNOSTIC APPARATUS

(71) Applicant: Toshiba Medical Systems Corporation, Otawara-shi (JP)

(72) Inventors: Jaeho Choi, Utsunomiya (JP); Yoshiyuki Sato, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 626 days.

(21) Appl. No.: 14/511,005

(22) Filed: Oct. 9, 2014

(65) Prior Publication Data
US 2015/0025337 A1    Jan. 22, 2015

Related U.S. Application Data

(63) Continuation of application No. PCT/JP2013/060831, filed on Apr. 10, 2013.

(30) Foreign Application Priority Data

Apr. 10, 2012  (JP) ................................. 2012-089520
Apr. 9, 2013   (JP) ................................. 2013-081536

(51) Int. Cl.
*A61B 8/00*   (2006.01)
*A61B 8/08*   (2006.01)

(52) U.S. Cl.
CPC ............ *A61B 8/543* (2013.01); *A61B 8/0883* (2013.01); *A61B 8/5207* (2013.01)

(58) Field of Classification Search
CPC ...... A61B 8/543; A61B 8/0883; A61B 8/5207
(Continued)

(56) References Cited

U.S. PATENT DOCUMENTS

| 6,544,175 B1 * | 4/2003 | Newman .................. A61B 8/00 600/437 |
| 2009/0192386 A1 * | 7/2009 | Hashimoto .............. A61B 8/00 600/443 |

FOREIGN PATENT DOCUMENTS

| CN | 101491448 A | 7/2009 |
| JP | 2005-270325 A | 10/2005 |

(Continued)

OTHER PUBLICATIONS

International Search Report dated Jul. 16, 2013 for PCT/JP2013/060831 filed on Apr. 10, 2013 with English Translation.

(Continued)

*Primary Examiner* — Sanjay Cattungal
(74) *Attorney, Agent, or Firm* — Oblon, McClelland, Maier & Neustadt, L.L.P.

(57) ABSTRACT

According to one embodiment, an ultrasonic diagnostic apparatus sets a desired period with reference to a predetermined time phase in each heartbeat of the object, sequentially executes ultrasonic scanning on a plurality of sub-volumes in a period including the diagnosis period to acquire sub-volume data corresponding to a plurality of time phases, controls acquisition timing of the sub-volume data from a time point elapsed from the predetermined time phase by a predetermined period of time while switching the sub-volume, generates composite sub-volume data or a full volume data constituted by a plurality of sub-volume data by performing combining processing of the sub-volume data acquired in the different diagnosis periods, detects at least one of a cyclic change of a heartbeat signal and a change in the number of sub-volume data acquired in the one diagnosis period and performs combining processing of sub-volume data based on a detection result.

13 Claims, 12 Drawing Sheets

(58) Field of Classification Search
USPC .................................................. 600/437–469
See application file for complete search history.

(56) References Cited

FOREIGN PATENT DOCUMENTS

| | | |
|---|---|---|
| JP | 2007-020908 A | 2/2007 |
| JP | 2008-104640 A | 5/2008 |
| JP | 2009-142600 A | 7/2009 |
| JP | 2009-172223 A | 8/2009 |
| JP | 2009-225948 A | 10/2009 |
| JP | 2009-240701 A | 10/2009 |

OTHER PUBLICATIONS

International Written Opinion dated Jul. 16, 2013 for PCT/JP2013/060831 filed on Apr. 10, 2013.
Combined Chinese Office Action and Search Report dated Jan. 6, 2015 in Patent Application No. 201380001881.2 (with English Translation of Category of Cited Documents).
International Preliminary Report of Patentability and Written Opinion dated Oct. 14, 2014 in PCT/JP2013/060831 (English translation only).

\* cited by examiner

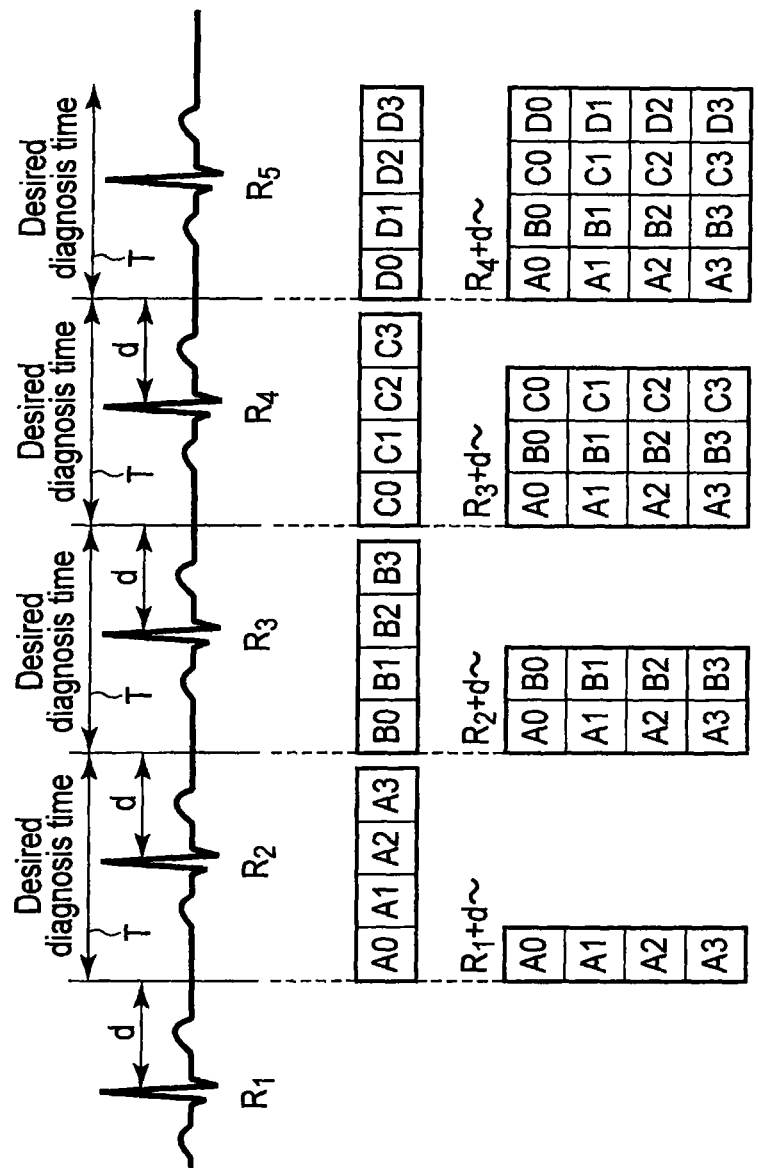
F I G. 7

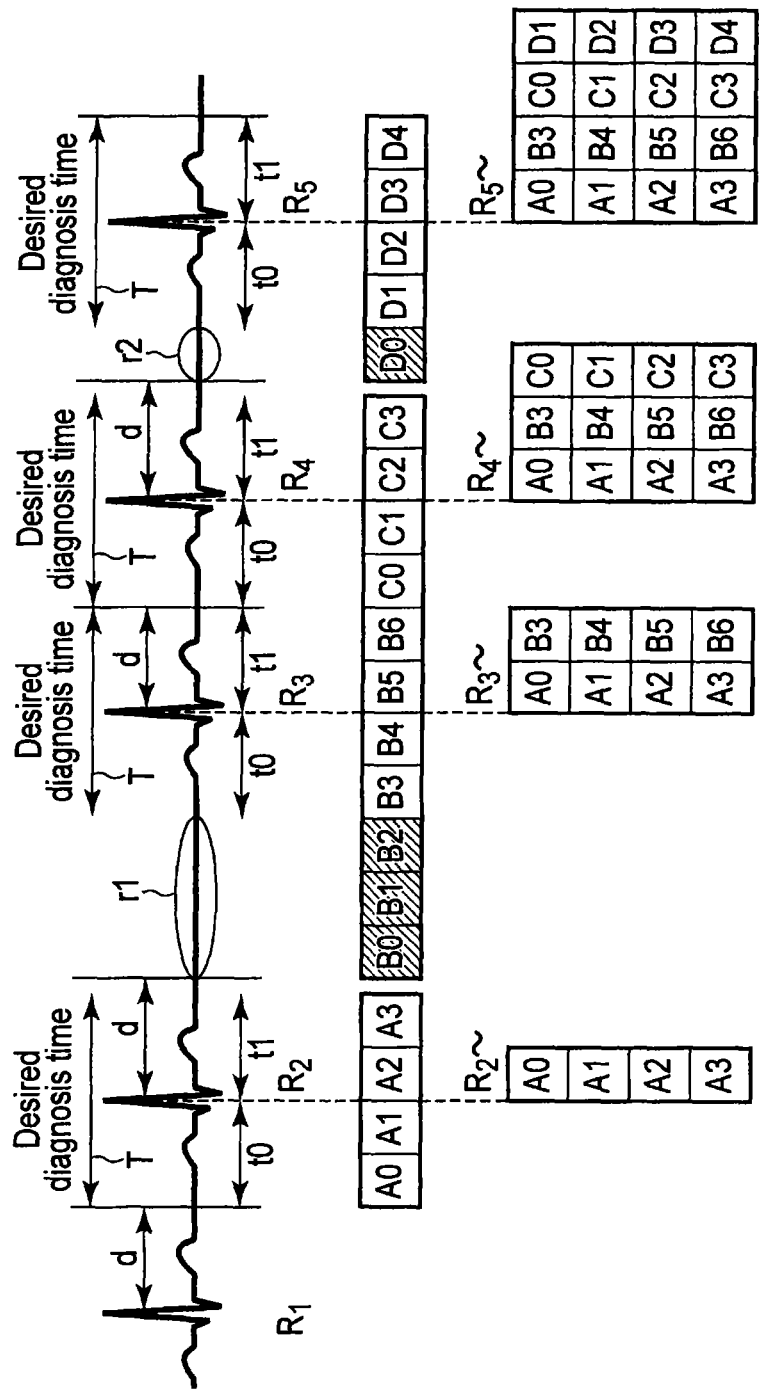
F I G. 13

ULTRASONIC DIAGNOSTIC APPARATUS, ULTRASONIC IMAGE PROCESSING APPARATUS, AND MEDICAL IMAGE DIAGNOSTIC APPARATUS

CROSS-REFERENCE TO RELATED APPLICATIONS

This application is a Continuation Application of PCT Application No. PCT/JP2013/060831, filed Apr. 10, 2013 and based upon and claiming the benefit of priority from the Japanese Patent Application No. 2012-089520, filed Apr. 10, 2012 and the Japanese Patent Application No. 2013-081536, filed Apr. 9, 2013, the entire contents of all of which are incorporated herein by reference.

FIELD

Embodiments described herein relate generally to an ultrasonic diagnostic apparatus, ultrasonic image processing apparatus, and medical image diagnostic apparatus which perform diagnosis by imaging the inside of the living body by ultrasonic waves or the like.

BACKGROUND

Recently, image diagnosis using a medical image diagnostic apparatus typified by an ultrasonic diagnostic apparatus, X-ray computed tomography apparatus, magnetic resonance imaging apparatus, and the like has an important role in clinical fields. For example, an ultrasonic diagnostic apparatus is an apparatus which applies ultrasonic pulses generated by the transducers provided in an ultrasonic probe into an object to be examined, and receives reflected ultrasonic waves generated by differences in acoustic impedance of the tissues of the object via the transducers, thereby acquiring biological information. This apparatus can perform real-time display of image data by the simple operation of bringing the ultrasonic probe into contact with the surface of the body, and hence is widely used for morphological diagnosis and functional diagnosis of various organs.

Recently, a system capable of high-speed acquisition and display of three-dimensional images has been rapidly developed, and hence has become capable of providing diagnostic images in different fields of view such as three-dimensional images and three-dimensional moving images.

On the other hand, image diagnosis using an ultrasonic diagnostic apparatus is image diagnosis using ultrasonic waves propagating in the living body. Even if, therefore, this apparatus is made compatible to three-dimensional images, there is a certain limitation on the number of scanning lines which the apparatus can transmit/receive per unit time. For this reason, various techniques have been attempted to scan a wide three-dimensional area with high resolution. When visualizing a wide region by using an ultrasonic diagnostic apparatus, the apparatus basically generates a three-dimensional image in a wide range by concatenating image data obtained by scanning three-dimensional spaces in small areas.

When, however, acquiring living body images, since some regions move due to respirations and the pulsations of the heart, it is necessary to acquire three-dimensional images in synchronism with these movements.

There is known a recently employed method of acquiring a plurality of small area three-dimensional moving images in synchronism with the movement of the heart and generating a three-dimensional moving image of the overall heart by combining the images. Such a method acquires and combines a plurality of small area three-dimensional moving images in synchronism with the movement of the heart. For example, image acquisition is often performed in synchronism with the movement of the heart by using biological signals such as ECG signals.

More specifically, this method divides the overall three-dimensional area of the heart to be observed with an ultrasonic diagnostic apparatus into a plurality of sub-volumes (e.g., four sub-volumes), and sequentially acquires data corresponding to one heartbeat concerning each sub-volume based on an ECG signal. In this data acquisition, for example, the method acquires data in the same time phases in a heartbeat cycle with reference to a position near an end-diastole at which an R wave is generated. The method then generates data corresponding to the three-dimensional area by combining the respective acquired sub-volume data so as to make the data in the same time phases spatially continuous.

Although each sub-volume corresponds to each area obtained by dividing a three-dimensional space, reconstructing data corresponding to spatially continuous three-dimensional areas can provide a three-dimensional image (to be referred to as a three-dimensional area moving image hereinafter) which looks as if moving images of the overall three-dimensional area of the heart to be observed were collected and displayed at once.

When using the above method, in order to visually recognize the three-dimensional area moving image obtained by combining the data of the respective sub-volumes as a single three-dimensional moving image, the respective sub-volumes need to be spatially continuous sub-volumes, and it is necessary to acquire data in the same time phases.

If, however, an object is, for example, an arrhythmic patient, when the heartbeat cycle is disturbed, the heartbeat period changes. As a consequence, the time phases of data acquired concerning the respective sub-volumes shift from each other. This makes it difficult to obtain a practical three-dimensional area moving image.

This embodiment has been made in consideration of the above problem, and has as its object to provide an ultrasonic diagnostic apparatus, ultrasonic image processing apparatus, and medical image diagnostic apparatus which present a three-dimensional area moving image obtained by combining data in the same time phases for the respective sub-volumes even if the heartbeat cycle or heartbeat period is disturbed as in a case in which, for example, an object is an arrhythmic patient.

BRIEF DESCRIPTION OF THE DRAWINGS

FIG. 7 is a sequence chart showing an example of scan processing and three-dimensional image combining processing in a "Delay Mode" by the ultrasonic diagnostic apparatus according to this embodiment.

FIG. 13 is a sequence chart showing scan processing and three-dimensional image combining processing in the "second correction mode".

DETAILED DESCRIPTION

In general, according to one embodiment, an ultrasonic diagnostic apparatus includes a heartbeat signal acquisition unit, a diagnosis period setting unit, a data acquisition unit, a data acquisition control unit, a combining processing unit, a heartbeat variation detection unit, and a combining processing control unit. The heartbeat signal acquisition unit configured to acquire a heartbeat signal of an object to be examined. The diagnosis period setting unit configured to set a desired period with reference to a predetermined time phase in one heartbeat as a diagnosis period in each heartbeat of the object. The data acquisition unit configured to sequentially execute ultrasonic scanning on a plurality of sub-volumes constituting a full volume as a diagnosis target area of the object in a period including the diagnosis period to acquire sub-volume data corresponding to a plurality of time phases concerning each of the sub-volumes and each of a plurality of heartbeats. The data acquisition control unit configured to control the data acquisition unit to start acquisition of the sub-volume data from a time point elapsed from the predetermined time phase by a predetermined period of time while switching the sub-volume as an ultrasonic scan target for the each heartbeat. The combining processing unit configured to generate composite sub-volume data or the full volume data constituted by a plurality of sub-volume data by performing combining processing of the sub-volume data acquired in the different diagnosis periods. The heartbeat variation detection unit configured to detect at least one of a cyclic change of a heartbeat signal of the object and a change in the number of sub-volume data acquired in the one diagnosis period. The combining processing control unit configured to control the combining processing unit so as to perform combining processing of sub-volume data based on a detection result obtained by the heartbeat variation detection unit.

An embodiment of the present invention will be described below with reference to the accompanying drawings. This embodiment can be applied to any of an ultrasonic diagnostic apparatus, an ultrasonic image processing apparatus, and a medical image diagnostic apparatus. For the sake of a concrete description, the embodiment will be applied to an ultrasonic diagnostic apparatus.

Figure 1:
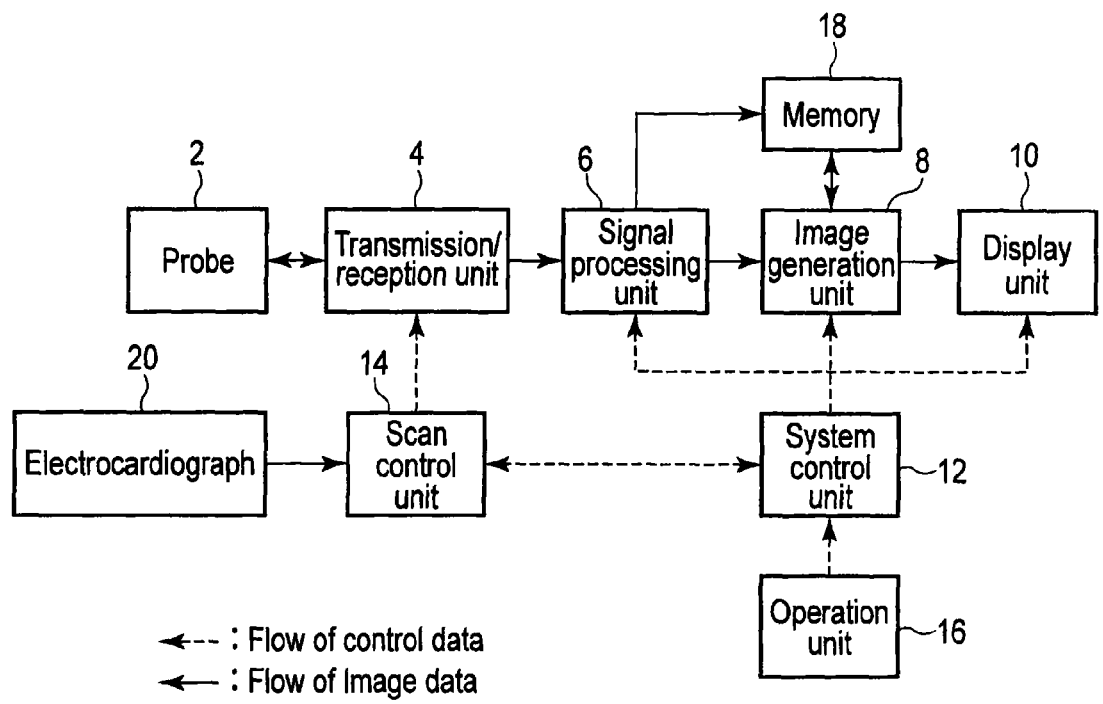
FIG. 1 is a block diagram showing an example of the arrangement of an ultrasonic diagnostic apparatus according to an embodiment of the present invention.

FIG. 1 is a block diagram showing an example of the arrangement of an ultrasonic diagnostic apparatus according to an embodiment of the present invention. As shown in FIG. 1, the ultrasonic diagnostic apparatus according to this embodiment includes an ultrasonic probe 2, a transmission/reception unit 4, a signal processing unit 6, an image generation unit 8, a display unit 10, a system control unit 12, a scan control unit 14, an operation unit 16, a memory 18, and an electrocardiograph 20.

The ultrasonic probe 2 is a device (probe) which transmits ultrasonic waves to an object, and receives reflected waves from the object based on the transmitted ultrasonic waves. The ultrasonic probe 2 has, on its distal end, an array of a plurality of piezoelectric transducers, a matching layer, a backing member, and the like. The piezoelectric transducers transmit ultrasonic waves in a desired direction in a scan area based on driving signals from the transmission/reception unit 4, and convert reflected waves from the object into electrical signals. The matching layer is an intermediate layer which is provided for the piezoelectric transducers to make ultrasonic energy efficiently propagate. The backing member prevents ultrasonic waves from propagating backward from the piezoelectric transducers.

When the ultrasonic probe 2 transmits an ultrasonic wave to an object, the transmitted ultrasonic wave is sequentially reflected by a discontinuity surface of acoustic impedance of internal body tissue, and is received as an echo signal by the ultrasonic probe 2. The amplitude of this echo signal depends on an acoustic impedance difference on the discontinuity surface by which the echo signal is reflected. The echo produced when a transmitted ultrasonic pulse is reflected by a moving blood flow is subjected to a frequency shift depending on the velocity component of the moving body in the ultrasonic transmission/reception direction by the Doppler effect.

The transmission/reception unit 4 includes a trigger generation circuit, a delay circuit, a pulser circuit, an amplifier circuit, an A/D converter, and an adder.

The transmission/reception unit 4 functions as a transmission unit in the following manner. The trigger generation circuit repetitively generates trigger pulses for the formation of transmission ultrasonic waves at a predetermined rate frequency fr Hz (period: 1/fr sec). The delay circuit gives each trigger pulse a delay time necessary to focus ultrasonic waves into a beam and determine transmission directivity for each channel. The pulser circuit applies a driving pulse to the ultrasonic probe 2 at the timing based on this trigger pulse. In this manner, the transmission/reception unit 4 causes the ultrasonic probe 2 to transmit a desired ultrasonic wave.

The transmission/reception unit 4 functions as a reception unit in the following manner. The amplifier circuit amplifies an echo signal (reflection signal) received via the probe 2 for each channel. The A/D converter converts each analog echo signal into a digital echo signal. The delay circuit gives the digitally converted echo signals delay times necessary to determine reception directivities and perform reception dynamic focusing. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The signal processing unit 6 includes a B-mode processing unit and a Doppler processing unit. The B-mode processing unit receives an echo signal from the transmission/reception unit 4, and performs logarithmic amplification, envelope detection processing, and the like for the signal to generate data whose signal intensity is expressed by a luminance level. This data is transmitted to the image generation unit 8 and is displayed as a B-mode image whose reflected wave intensity is expressed by a luminance on the display unit 10. The Doppler processing unit extracts a blood flow signal from the echo signal received from the transmission/reception unit 4, and generates blood flow data. In general, the Doppler processing unit extracts a blood flow by CFM (Color Flow Mapping). In this case, the Doppler processing unit analyzes the blood flow signal to obtain blood flow information such as mean velocities, variances, and powers as blood flow data at multiple points. The signal processing unit 6 also generates image data concerning a sub-volume (to be referred to as sub-volume data hereinafter) by using the raw data generated by the above processing.

The image generation unit 8 generates an ultrasonic diagnostic image as a display image based on various types of data output from the signal processing unit 6. The image generation unit 8 executes predetermined image processing such as volume rendering by using the sub-volume data output from the signal processing unit 6. That is, the image generation unit 8 spatially concatenates (combines) sub-volume data, of a plurality of sub-volume data, which coincide in "time phase (to be described in detail later)" to generate a plurality of sub-volume data corresponding to the respective time phases. The image generation unit 8 then combines full volume data with character information of various types of parameters, scale marks, and the like and outputs the resultant data as a video signal to the display unit 10. This causes the display unit 10 to display a three-dimensional area moving image concerning a diagnosis target area (visualization target area).

In this case, a "time phase" represents a delay amount from a predetermined time point as a reference time point such as a time point when a trigger signal to start scan processing is generated. That is, data in the same time phase are those acquired at the time point elapsed from the reference time point by the same delay amount (the same time).

Note that, in addition to a "time phase", a concept called a "phase" exists. A "phase" represents a position during the action of the heart which is actually moving almost periodically. Combining sub-volume data in the same time phases can obtain full volume data constituted by the sub-volume data coinciding in time phase.

Note that data before it is input to the image generation unit 8 is sometimes called "raw data".

The display unit 10 is a display device formed from, for example, a liquid display device, and displays the data output from the image generation unit 8, various types of diagnostic parameters, and the like.

The system control unit 12 comprehensively controls the overall ultrasonic diagnostic apparatus based on the diagnostic mode set by the operation unit 16, various types of parameters, and the like. The system control unit 12 includes a ROM storing a program for implementing a three-dimensional trigger scan and a control program for implementing image generation/display and the like. The system control unit 12 reads out these programs from the ROM, expands the programs in its own memory, and executes computation, control, and the like associated with each type of processing.

The scan control unit 14 supplies a pulse repetition frequency, transmission/reception position information, and the like to the transmission/reception unit 4 in accordance with a designated beam count, frame count, frame rate, and the like under the control of the system control unit 12. The scan control unit 14 generates a trigger signal based on the ECG signal output from the electrocardiograph 20, decides various factors associated with the beam scan position for each sub-volume and repeated scanning in each sub-volume in synchronism with the trigger signal, and outputs the factors to the transmission/reception unit 4 and the image generation unit 8.

The operation unit 16 is also called a Man-Machine Interface which is operated to, for example, set various types of diagnostic modes and various types of parameters associated with the diagnostic modes for the ultrasonic diagnostic apparatus.

The memory 18 is a memory for recording the data output from the signal processing unit 6 and outputs the data to be recorded to the image generation unit 8 in accordance with an instruction from the image generation unit 8.

The electrocardiograph 20 is a measurement member for acquiring a signal having an electrocardiographic waveform synchronous with the movement of the heart, i.e., an ECG (Electro Cardio Gram) signal, and outputs the acquired ECG signal to the scan control unit 14. In a general triggered three-dimensional diagnostic mode, the apparatus acquires sub-volume data by changing a scan range for each heartbeat period (switching sub-volumes) by using an R wave of an ECG signal as a trigger signal, combines the data, and displays the resultant data. The apparatus often sets the number of volume data constituting full volume data and the number of data to be acquired in one sub-volume in one heartbeat period in accordance with the heart rate of an object (the highest heart rate) or the like.

Figure 2:
FIG. 2 is a view showing an example of the waveform of a typical ECG signal.
Figure 3:
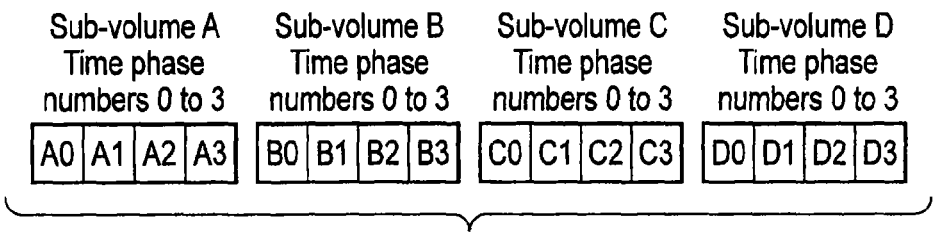
FIG. 3 is a view showing an example of the arrangement of sub-volume data.
Figures 4, 5:
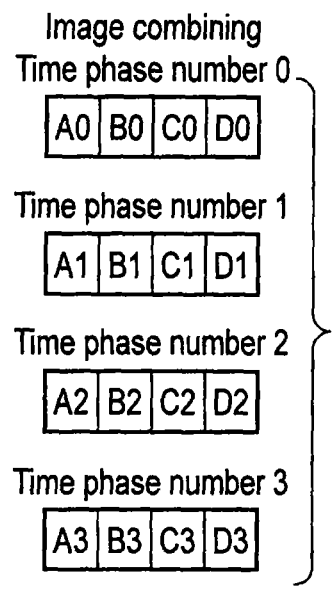
FIG. 4 is a view showing an example of the arrangement of full volume data.
FIG. 5 is a view showing an example of a method of displaying sub-volume data.
Figure 6:
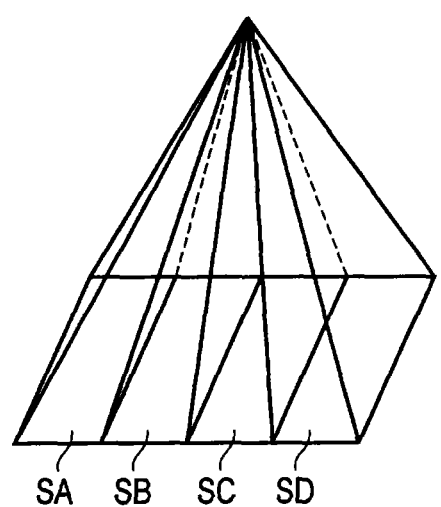
FIG. 6 is a view showing an example of the arrangement of full volume data.

An example of scan processing and three-dimensional image combining processing in the "triggered three-dimensional diagnostic mode" of the ultrasonic diagnostic apparatus according to this embodiment will be described with reference to FIGS. 2, 3, 4, 5, and 6. FIG. 2 is a view showing an example of the waveform of a typical ECG signal. FIG. 3 is a view showing an example of the arrangement of sub-volume data. FIG. 4 is a view showing an example of the arrangement of full volume data. FIG. 5 is a view showing an example of a method of displaying sub-volume data. FIG. 6 is a view showing an example of the arrangement of full volume data.

As shown in FIG. 2, an R wave appears in a predetermined cycle in the waveform of the ECG signal output from the electrocardiograph 20. In a general triggered three-dimensional diagnostic mode, this R wave is used as a trigger signal. That is, in the general triggered three-dimensional diagnostic mode, as shown in FIG. 3, the apparatus acquires image data corresponding to one heartbeat (sub-volume data) for every n (n=4 in this case) sub-volumes constituting the overall three-dimensional area (full volume) of the heart as an observation target at a timing synchronous with an R wave as a trigger signal (or a predetermined time point with reference to an R wave).

The apparatus then concatenates (combines) the respective sub-volume data to generate full volume data. When performing this combining operation, as shown in FIG. 4, the apparatus generates full volume data by extracting sub-volume data in the same "time phases" from the respective sub-volume data of a plurality of frames and concatenating (combining) the sub-volume data.

As a method of displaying sub-volume data and the full volume data constituted by them, there is available a method of sequentially displaying sub-volume data in the order of generation, as shown in FIG. 5. According to this display method, the apparatus acquires and sequentially displays sub-volume data corresponding to m time phases (m=4 in this case) concerning a sub-volume A after time $R_1$ (the time point when an nth R wave $R_n$ is detected will be referred to as time $R_n$). In the subsequent heartbeat periods (heartbeat periods corresponding to times $R_2$, $R_3$, $R_4$, ..., $R_n$), the apparatus combines and displays sub-volume data corresponding to the m time phases concerning the sub-volumes which have already been acquired.

With above processing, it is possible to obtain full volume data concerning the entire range as a diagnosis target by combining the sub-volume data obtained by scanning sub-volumes SA, SB, SC, and SD at a high frame rate, as shown in FIG. 6.

The following is an example of scan processing and three-dimensional image combining processing in a "Delay Mode" by the ultrasonic diagnostic apparatus according to this embodiment. FIG. 7 is a sequence chart showing an example of scan processing and three-dimensional image combining processing in the "Delay Mode" by the ultrasonic diagnostic apparatus according to this embodiment.

The "Delay Mode" is a mode allowing to acquire and display full volume data in a desired time zone centered on the detection time point of an R wave. In this "Delay Mode", as shown in FIG. 7, the apparatus sets, as the start time point of scan processing, the time point elapsed (delayed) from the time point when an R wave is detected by a delay time d instead of setting the time point when an R wave is detected as the start time point of scan processing.

In the case shown in FIG. 7, the apparatus acquires sub-volume data corresponding to "four phases (m=4)" concerning each sub-volume. That is, in the case shown in FIG. 7, the apparatus acquires sub-volume data corresponding to four time phases (two time phases before the detection time point of an R wave and two time phases after the detection time point) from the time point elapsed from the detection time point (the occurrence time point) of an R wave by the time d. The apparatus then sequentially displays, in real time, the sub-volume data acquired in a desired diagnosis time T corresponding to $R_{(n+1)}$ as the (n+1)th R wave from time $R_n$+d which is the time point elapsed from time $R_n$ by the delay time d. In this case, if there are any sub-volume data acquired in the desired diagnosis time T corresponding to the R wave detected before $R_{(n+1)}$ which is the (n+1)th R wave, the apparatus combines and displays the sub-volume data in the same time phases.

That is, as shown in FIG. 7, in this case, the time point elapsed from the time when an R wave is detected by d is set as the start time point of scan processing. The apparatus performs scan processing so as to acquire a desired number (corresponding to desired time phases) of sub-volume data from this start time point. In other words, the apparatus performs scan processing for the predetermined desired diagnosis time T from the start time point.

Using the "Delay Mode" described above makes it possible to acquire full volume data in a desired time zone (desired diagnosis time T) centered on the detection time point of an R wave and perform three-dimensional image combining processing for the data. If, however, an object is an arrhythmic patient or the like and a heartbeat cycle or heartbeat period is disturbed, the following problem may arise.

Figure 8:
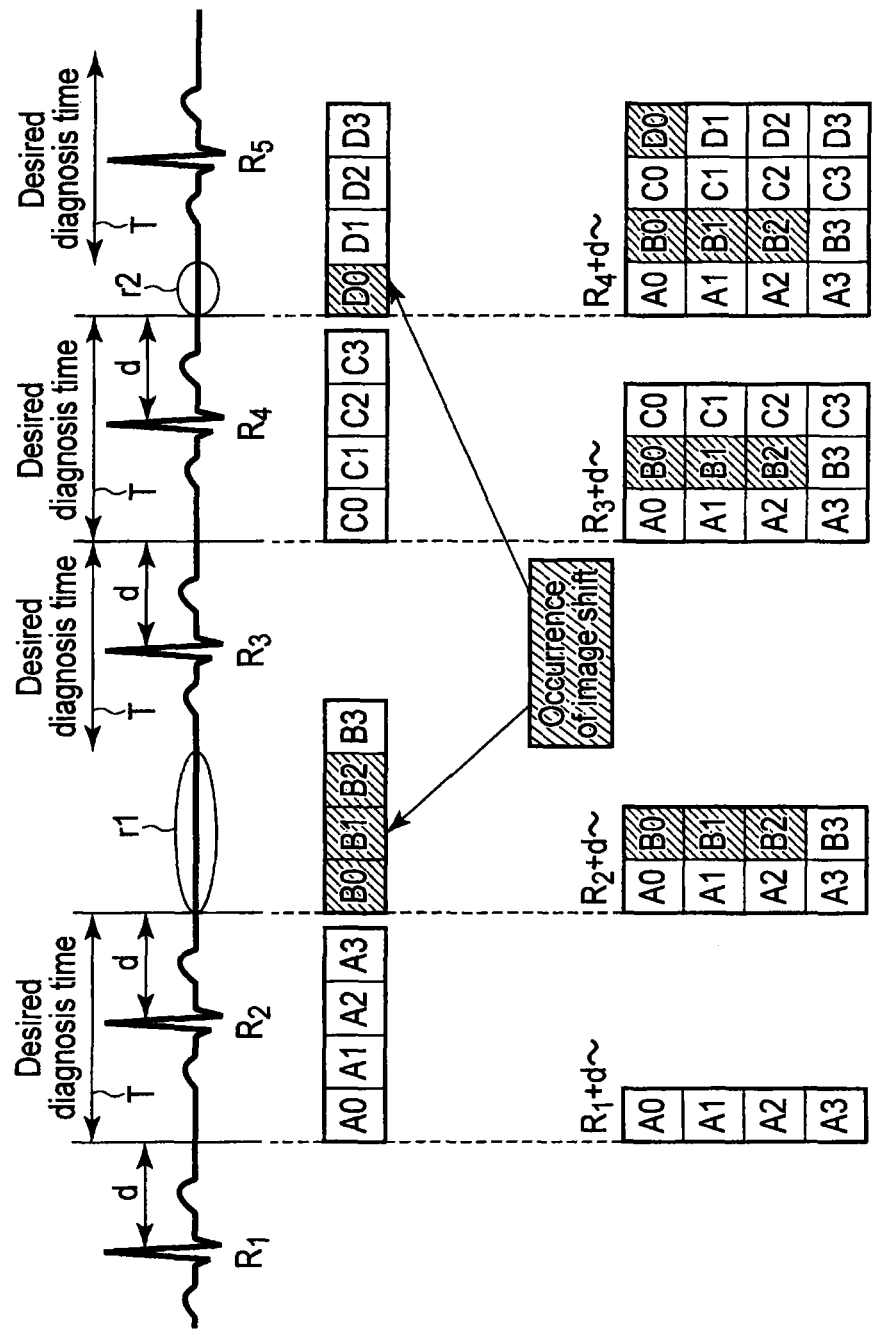
FIG. 8 is a sequence chart showing an example of scan processing and three-dimensional image combining processing when an object is an arrhythmic patient.

FIG. 8 is a sequence chart showing an example of scan processing and three-dimensional image combining processing when an object is an arrhythmic patient. In the case shown in FIG. 8, the interval between $R_2$ and $R_3$ is a time longer than usual. In such a case, the apparatus performs scan processing in heartbeat disturbance times r1 and r2 shown in FIG. 8 and acquires sub-volume data in the heartbeat disturbance times r1 and r2 (sub-volume data $B_0$, $B_1$, $B_2$, and $D_0$).

As a consequence, the apparatus acquires sub-volume data in a phase totally different from sub-volume data acquired in another desired diagnosis time T due to a heartbeat cycle disturbance instead of acquiring the same numbers of sub-volume data before and after the detection time (occurrence time; ditto for the following) of an R wave. These data are then provided for three-dimensional image combining processing. That is, when generating full volume data by combining sub-volume data, the apparatus combines sub-volume data in different time phases/phases.

That is, when a heartbeat cycle or heartbeat period is disturbed, full volume data generated by combining processing without any correction includes sub-volume data which differ in phase, resulting in data unsuitable as data used for image diagnosis.

The following is a description about scan processing and three-dimensional image combining processing (to be referred to as "correction mode") which can obtain full volume data suitable for image diagnosis even when a heartbeat cycle or heartbeat period is disturbed.

<<First Correction Mode>>

Figure 9:
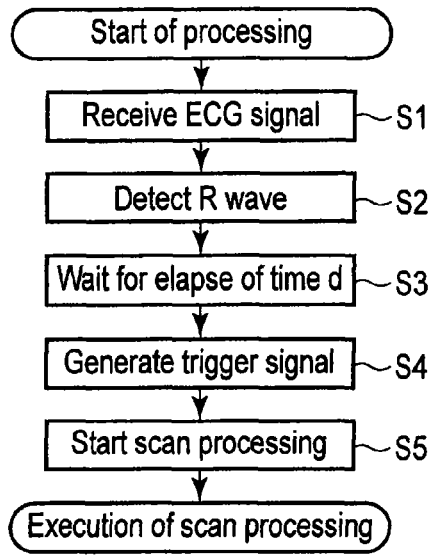
FIG. 9 is a flowchart associated with scan processing in a "first correction mode".
Figure 10:
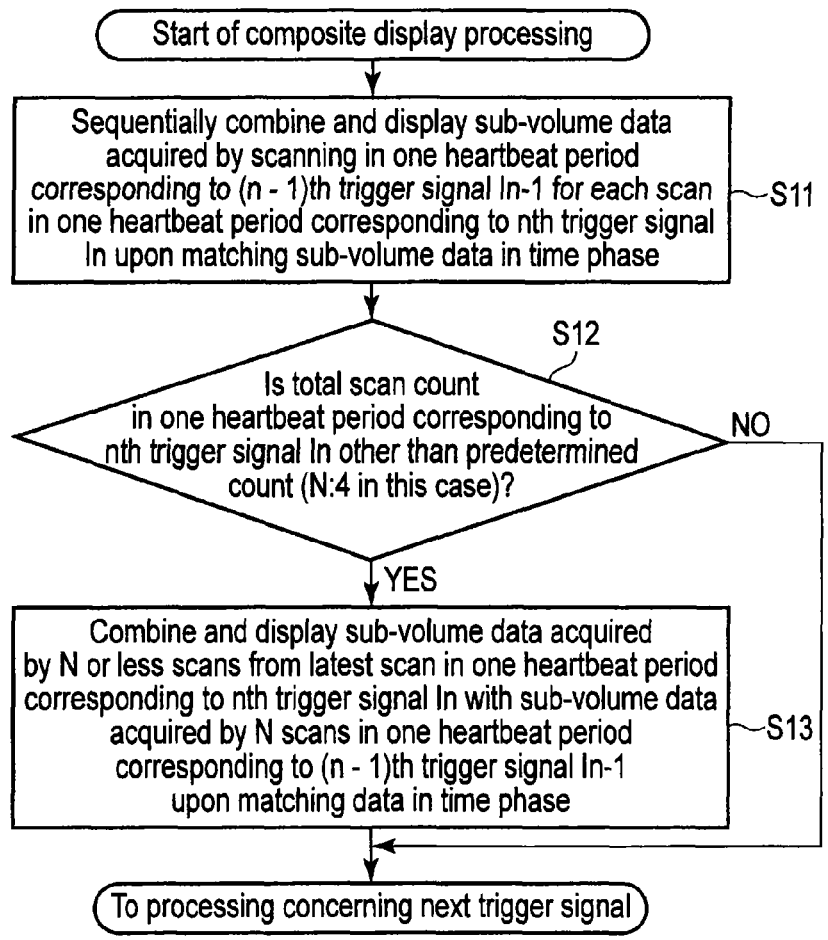
FIG. 10 is a flowchart associated with three-dimensional image combining processing in the "first correction mode".
Figure 11:
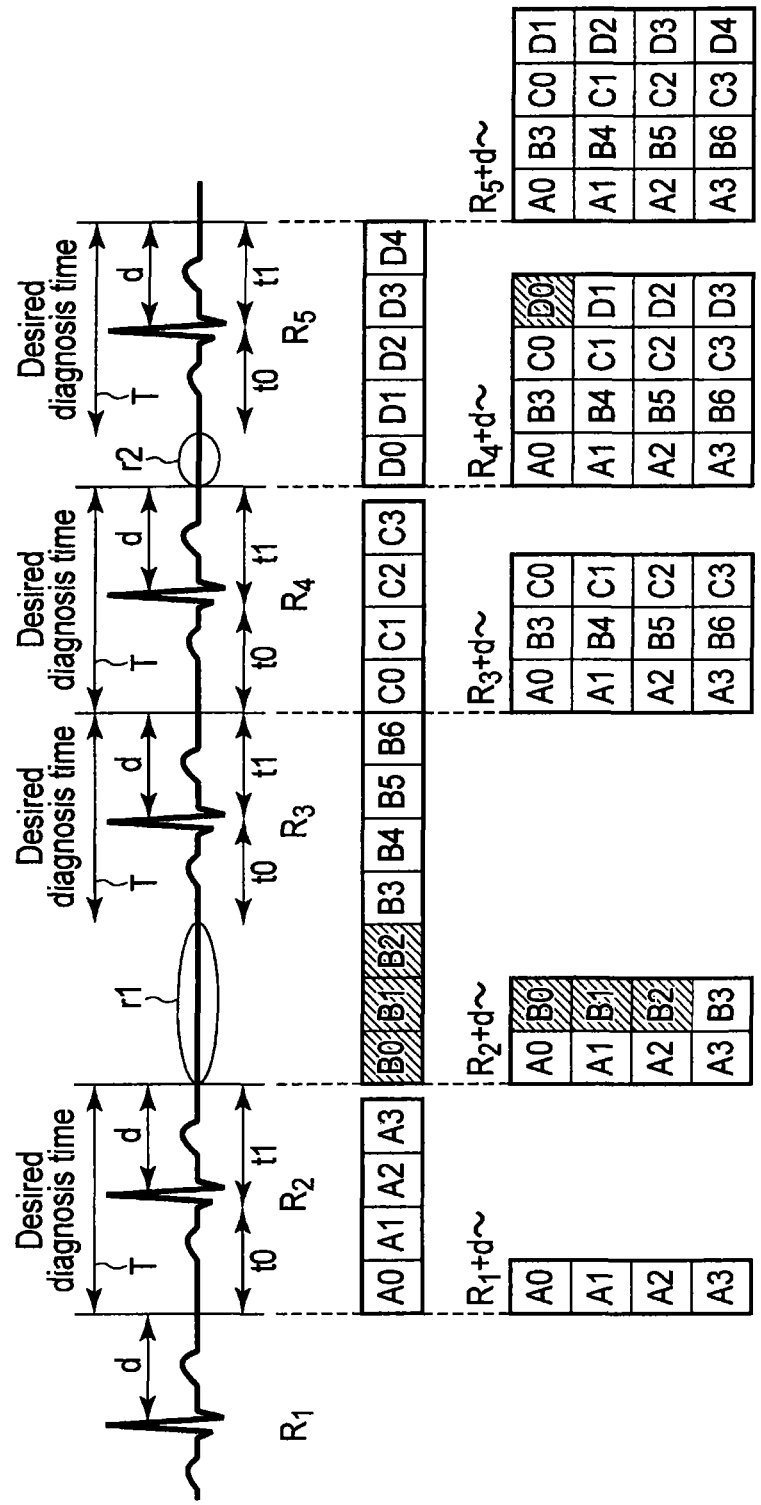
FIG. 11 is a sequence chart showing scan processing and three-dimensional image combining processing in the "first correction mode".

FIG. 9 is a flowchart associated with scan processing in the "first correction mode". FIG. 10 is a flowchart associated with three-dimensional image combining processing in the "first correction mode". FIG. 11 is a sequence chart showing scan processing and three-dimensional image combining processing in the "first correction mode".

In this case, the apparatus executes scan processing for each of four sub-volumes (sub-volumes A, B, C, and D) constituting a full volume throughout the desired diagnosis time T. In addition, assume that the desired diagnosis time T during which the apparatus executes scan processing for one sub-volume is at least a time almost equal to or more than a motion cycle of a diagnostic region (a heartbeat cycle in this case).

When setting m time phases for each motion cycle of a diagnostic region in the desired diagnosis time T, the apparatus acquires (m) sub-volume data corresponding to at least m time phases for the respective sub-volume data (sub-volume data A, B, C, and D).

The electrocardiograph 20 outputs an ECG signal to the scan control unit 14 (step S1). Subsequently, the scan control unit 14 detects an R wave from the ECG signal (step S2). In this case, the scan control unit 14 waits for the lapse of the delay time d as shown in FIG. 11 (step S3). The value of the delay time d depends on the value of the desired diagnosis time T (in other words, the number of sub-volume data acquired).

In the "first correction mode", the apparatus uses sub-volume data acquired by executing scan processing for the same times before and after the detection time of an R wave to generate full volume data.

As shown in FIG. 11, a scan time before the detection time of an R wave is called a first scan time t0, and a scan time after the detection of the R wave is called a second scan time t1. Like the value of the delay time d, the values of the times t0 and t1 also depend on the number of sub-volume data (in other words, the length of the desired diagnosis time T) obtained in the desired diagnosis time T.

That is, the values of the delay time d, the first scan time t0, and the second scan time t1 are determined in accordance with the desired diagnosis time T or the desired number of sub-volume data to be acquired. In practice, the value of the delay time d is equal to the value of the second scan time t1. In addition, obviously, the value of the first scan time t0 may be equal to the value of the delay time d and the value of the second time t1.

The user sets the values of the desired diagnosis time T, the first scan time t0, the second scan time t1, and the delay time d by using the operation unit 16. Note that the apparatus may be separately provided with a GUI for facilitating making these settings. Since the user can set these values to arbitrary values, he/she can designate a desired time zone (a desired interval) in an ECG signal and cause the display unit 10 to display an image in the designated time zone (interval).

In the case shown in FIG. 11, the interval from the time preceding the detection time of an R wave by the first scan time t0 to the time succeeding the same detection time by the second scan time t1 may be set as the desired diagnosis time T in the time zone (interval) of a display target. In the case shown in FIG. 11, the first scan time t0 and the second scan time t1 are set to the same time. However, the first scan time t0 and the second scan time t1 may be set to difference values.

The scan control unit 14 generates a trigger signal for the execution of scan processing at the time point elapsed from the time an R wave is detected upon completion of the processing in steps S1 and S2 described above by the time d (step S4). The scan control unit 14 decides conditions concerning a beam scan position for each sub-volume and repeated scanning in each sub-volume in synchronism with a trigger signal, and controls the transmission/reception unit 4 based on these conditions to start scan processing (step S5).

As described above, in the "first correction mode", as shown in FIG. 11, the time point elapsed (delayed) from the time point when an R wave is detected by the delay time d is set as the start time point of scan processing as in the case of the "Delay Mode". However, the end time point of scan processing differs from that in the "Delay Mode".

That is, in the "Delay Mode", the time point when the acquisition of the preset desired number of sub-volume data is complete from the start time point of scan processing (in other words, the time point when scan processing is executed for the desired diagnosis time T from the start time point of scan processing) is the end time point of the scan processing.

In the "first correction mode", the apparatus keeps executing scan processing from the time point elapsed from the time when an R wave is detected by d, as the start time point of the scan processing, to the start time point of the next scan processing.

That is, in the "first correction mode", the apparatus keeps executing the scan processing until the start time point of the next scan processing regardless of whether the scan processing of acquiring a desired number of sub-volume data from the start time point is complete (in other words, whether scan processing is executed for the predetermined desired diagnosis time T from the start time point), and stores the sub-volume data acquired by the scan processing in the memory 18.

Acquiring sub-volume data in this manner can secure desired numbers (two in this case) of sub-volume data before and after the time when an R wave is detected, even if a heartbeat period is disturbed. In other words, it is possible to secure the same scan processing time before and after the time when an R wave is detected.

Three-dimensional image combining processing in the "first correction mode" will be described with reference to FIGS. 10 and 11.

First of all, every time acquiring sub-volume data by scanning at the desired diagnosis time T corresponding to an nth trigger signal In, the system control unit 12 controls the respective units to sequentially combine the sub-volume data with the sub-volume data acquired by scanning in the desired diagnosis time T corresponding to the (n−1)th trigger signal I (n−1) while matching them in time phase and display the resultant data in real time (step S11).

In the case shown in FIG. 11, the display implemented by step S11 corresponds to display from time ($R_2$+d) to time ($R_3$+d) (composite display of sub-volume data A0 to A3 and sub-volume data B0 to B3) and display from time ($R_4$+d) to time ($R_5$+d) (composite display of sub-volume data A0 to A3, sub-volume data B0 to B3, sub-volume data C0 to C3, and sub-volume data D0 to D3).

In this case, the sub-volume data B0 to B2 are the data acquired in the heartbeat disturbance time r1, and the sub-volume data D0 is the data acquired in the heartbeat disturbance time r2. In this manner, the apparatus temporarily displays even the sub-volume data acquired in the heartbeat disturbance times r1 and r2 (the sub-volume data B0, B1, B2, and D0 in the case shown in FIG. 11) in real time upon matching the data in time phase with the sub-volume data acquired in the previous desired diagnosis time T.

The image generated and displayed in real time in this manner is based on composite sub-volume data obtained by combining sub-volume data which do not strictly match in cardiac time phase. The actually displayed image therefore becomes an unnatural image for the observer. This allows the observer to visually recognize the occurrence of disturbances of a heartbeat cycle/heartbeat period in real time by observing the image based on the sub-volume data acquired in the heartbeat disturbance times r1 and r2.

Subsequently, the system control unit 12 determines whether the "total scan count" (the number of scans for one sub-volume) in the desired diagnosis time T corresponding to the nth ECG trigger signal In is equal to or more than a predetermined scan count N (corresponding to predetermined time phases; N=4 in this case) in the desired diagnosis time T (step S12).

If YES in step S12, the system control unit 12 controls the respective units to display N sub-volume data acquired by N or less scans counted from the last scan in the desired diagnosis time T corresponding to the nth trigger signal In upon combining the data with the sub-volume data acquired by N scans in the desired diagnosis time T corresponding to the (n−1)th trigger signal I(n−1) while matching them in time phase (step S13).

In the case shown in FIG. 11, the display implemented by step S13 corresponds to display from time ($R_3$+d) to time ($R_4$+d) (composite display of sub-volume data A0 to A3, sub-volume data B3 to B6, and sub-volume data C0 to C3) and display from time ($R_5$+d) to time ($R_6$+d) (composite display of sub-volume data A0 to A3, sub-volume data B3 to B6, sub-volume data C0 to C3, and sub-volume data D1 to D4).

In this manner, the apparatus combines only the sub-volume data normally acquired in each desired diagnosis time T (the sub-volume data acquired in the first scan time t0 and the second scan time t1 concerning each R wave) without using any sub-volume data acquired in the heartbeat disturbance times r1 and r2 (the sub-volume data B0, B1, B2, and D0 in the case shown in FIG. 11) for combining processing and display.

When the processing in step S13 is complete or NO is obtained in step S12, the apparatus starts similar processing concerning the next trigger signal.

As described above, even if a heartbeat cycle/heartbeat period has been disturbed, the apparatus sequentially performs, with the processing in steps S11 to S13, combining processing by also using the sub-volume data acquired in the heartbeat disturbance times and displays the resultant data in real time while performing combining processing and display (to be referred to as "correction display") again for the same sub-volumes by using the sub-volume data acquired in the first scan time t0 and the second scan time t1 immediately after the end of the heartbeat disturbance times.

In the case shown in FIG. 11, data concerning a sub-volume B exhibit a motion shift relative to the adjacent sub-volume data at time ($R_2$+d), but the apparatus displays data without the "shift" at time ($R_3$+d). Likewise, in the case shown in FIG. 11, data concerning a sub-volume D exhibit a motion shift relative to the adjacent sub-volume data at time ($R_4$+d), but the apparatus displays data without the "shift" at time ($R_5$+d).

As described above, in the first correction mode, the time point elapsed from the detection time point of an R wave by the time d is set as the "start time of scan processing", and the apparatus keeps executing scan processing in the interval between the "start time of scan processing" and the next "start time of the scan processing".

That is, the apparatus keeps executing acquisition in the above period without specifying (limiting) the number of sub-volumes acquired in the desired diagnosis time T, sequentially uses sub-volume data for "real-time display" from the start time point of acquisition, and uses, for "correction display", sub-volume data corresponding to time phases going back from the end time point of acquisition.

As described above, according to the first correction mode, even if a heartbeat cycle or heartbeat period is disturbed as in a case in which an object is an arrhythmic patient, it is possible to present a three-dimensional area moving image obtained by combining data in the same time phases for the respective sub-volumes in real time.

More specifically, the first correction mode can provide the special effect of allowing, even if a heartbeat cycle/heartbeat period is disturbed in an object, the user to recognize the occurrence of the disturbance of the heartbeat cycle/heartbeat period of the object in real time and visually recognize a full volume image suitable for diagnosis immediately after the recognition.

<<Second Correction Mode>>

Scan processing and three-dimensional image combining processing in the "second correction mode" will be described below. To avoid a redundant description, differences from the "first correction mode" will be described.

Figure 12:
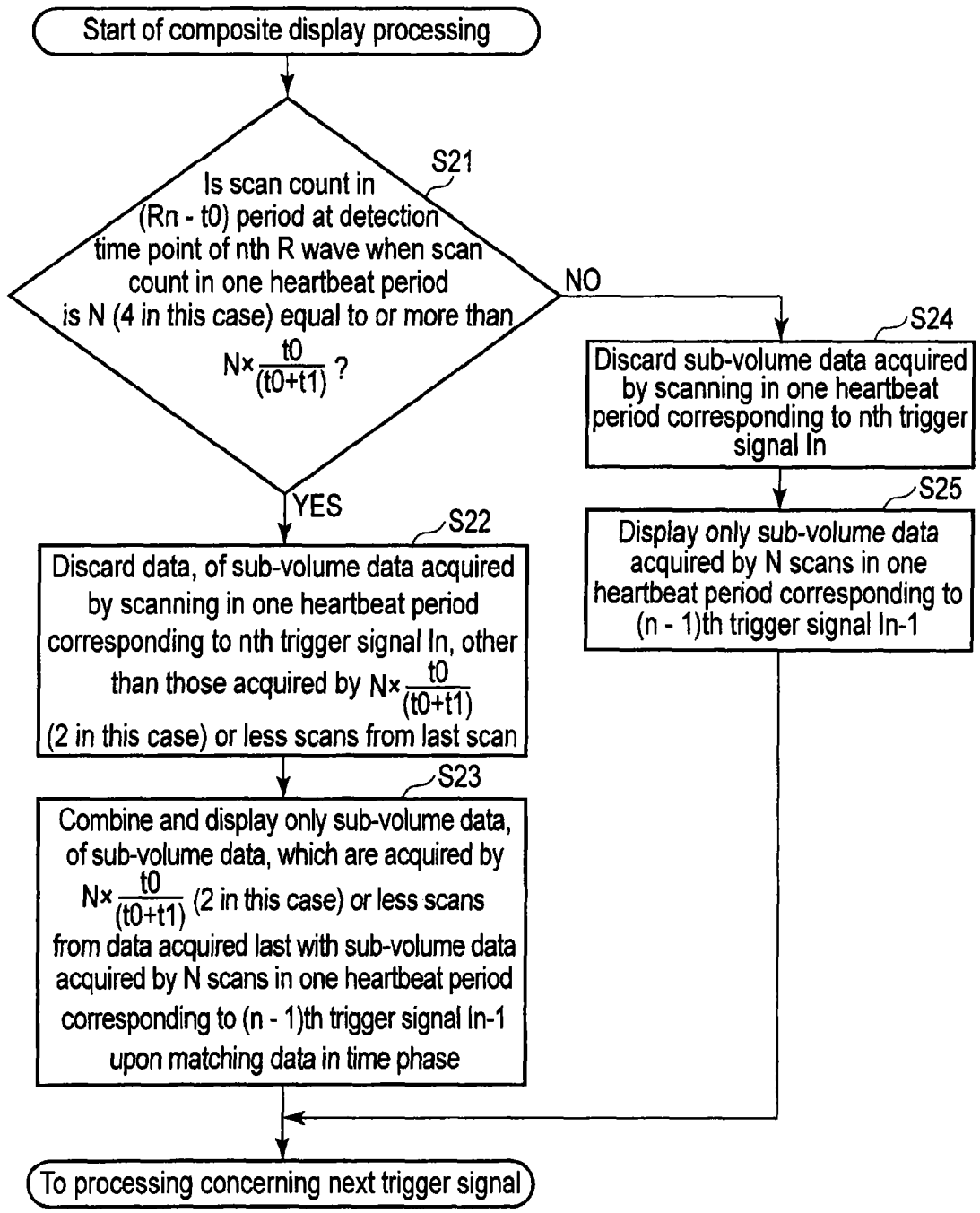
FIG. 12 is a flowchart associated with three-dimensional image combining processing in a "second correction mode".
Figure 14:
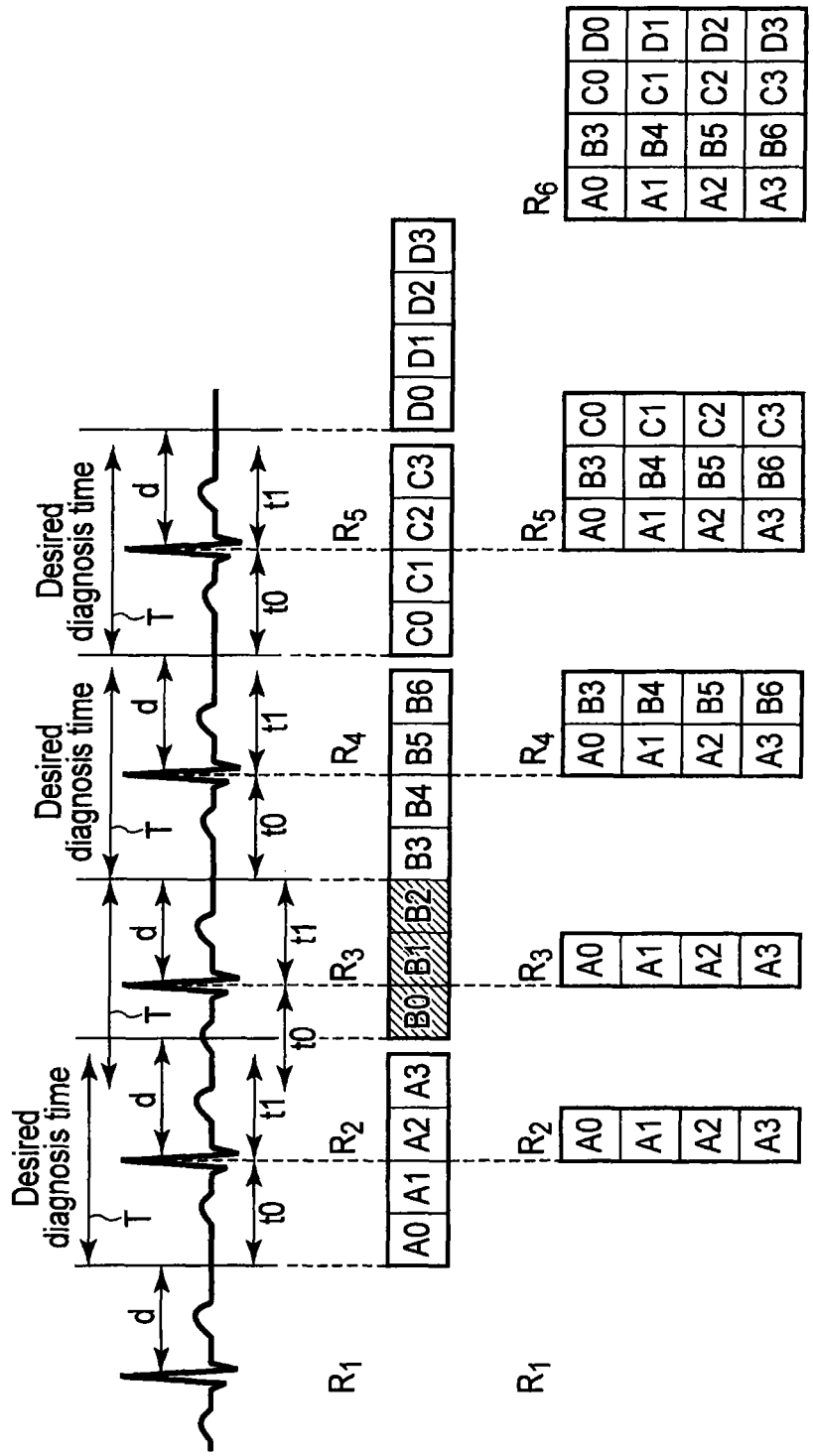
FIG. 14 is a sequence chart showing scan processing and three-dimensional image combining processing in the "second correction mode".

FIG. 12 is a flowchart according to three-dimensional image combining processing in the "second correction mode". FIGS. 13 and 14 each are a sequence chart showing scan processing and three-dimensional image combining processing in the "second correction mode". Note that scan processing in the "second correction mode" is the same as that in the "first correction mode" described with reference to FIG. 9.

Note that in the "first correction mode", when performing display in the desired diagnosis time T corresponding to the nth R wave (i.e., display of the data acquired in the desired diagnosis time T corresponding to the (n−1)th trigger signal I(n−1)), the apparatus performs real-time display from time $R_n$−t0 (the time point when data are acquired) and performs correction display at time $R_n$+d. In contrast to this, in the "second correction mode", the apparatus displays data corresponding to the nth R wave from time $R_n$ (the detection time point of an R wave). In the "second correction mode", therefore, the apparatus displays the sub-volume data acquired in the first scan time t0 with a slight delay from real-time display in a strict sense.

First of all, when the scan count in one desired diagnosis time T is N (N=4 in this case), the system control unit 12 determines, at the detection time point of $R_n$, which is the nth R wave, whether the scan count in the interval from the detection time point to the time going back from it by the time t0 (i.e., the scan count in the interval of ($R_n$−t0)) is equal to or more than N×t0/(t0+t1) (4×1/2=2 in this case) (step S21). In this case, t0=t1 and N=4.

Note that in step S21, the apparatus may determine the elapse of a scan time corresponding to a reference scan count instead of determining a scan count. In this case, the apparatus determines in step S21 whether the interval between R waves (R-R interval) is equal to or more than time t0+time t1 (whether the current state is a so-called "Early Trigger" state). In this case, if the R-R interval is equal to or more than time t0+time t1, YES is obtained in step S21. If the R-R interval is less than t0+t1, NO is obtained in step S21.

If YES is obtained in step S21, the system control unit 12 deletes, from the memory 18, data, of the sub-volume data acquired by scanning in the desired diagnosis time T corresponding to the nth trigger signal In, other than those acquired by N×t0/(t0+t1) (4×1/2=2 in this case) or less scans from the last scan (step S22).

Furthermore, the system control unit 12 performs control to display, in real time, only sub-volume data, of the sub-volume data acquired by scanning in the desired diagnosis time T corresponding to the nth trigger signal In, which are acquired by N×t0/(t0+t1) (4×1/2=2 in this case) or less scans from the last scan, upon combining the sub-volume data acquired by N scans in the desired diagnosis time T corresponding to the (n−1)th trigger signal I(n−1) while matching them in time phase (step S23).

The state set when YES is obtained in step S21 in this manner corresponds to states at times $R_3$ and $R_5$ in the case shown in FIG. 13. That is, the scan count in the desired diagnosis time T at time $R_3$ is five (>N×t0/(t0+t1) (4×1/2=2 in this case), and hence the process shifts from step S21 to step S22 to delete the sub-volume data B0, B1, and B2 from the memory 18 and combine the sub-volume data A0 to A3 with the sub-volume data B3 to B6.

Likewise, the scan count in the desired diagnosis time T at time $R_5$ is three (>N×t0/(t0+t1) (4×1/2=2 in this case), and hence the process shifts from step S21 to step S22 to delete the sub-volume data D0 from the memory 18, combine the sub-volume data A0 to A3, the sub-volume data B3 to B6, the sub-volume data C0 to C3, and the sub-volume data D1 to D4, and display the resultant data.

If it is not possible to perform N scans in one desired diagnosis time T, NO is obtained in step S21, and the system control unit 12 deletes sub-volume data acquired in the desired diagnosis time T and stored in the memory 18 (step S24). The state set when NO is obtained in step S21 corresponds to a state concerning the desired diagnosis time T corresponding to time $R_3$ in the case shown in FIG. 14. Note that the apparatus may delete no sub-volume data stored in the memory 18 in step S24, and may make setting not to use the sub-volume data for the subsequent processing.

Upon completing the processing in step S24, the system control unit 12 displays only the sub-volume data acquired by N scans in the desired diagnosis time T corresponding to the (n−1)th trigger signal I(n−1) (step S25).

The state set when NO is obtained in step S21 corresponds to a state at time $R_3$ in the case shown in FIG. 14. In this case, since the scan count in the desired diagnosis time T at time $R_3$ is one (<N×t0/t1) (4×1/2=2 in this case)), the system control unit 12 performs control to shift the process from step S21 to step S24 to delete the sub-volume data B0 from the memory 18 and display only the sub-volume data A0 to A3.

Upon completing the processing in step S23 and the processing in step S25, the apparatus starts similar processing concerning the next trigger signal. Note that upon performing the processing in step S25 (deleting the sub-volume data acquired by scanning in the desired diagnosis time T corresponding to the nth trigger signal In from the memory 18), the apparatus scans the same sub-volume (the sub-volume B in the case shown in FIG. 14) again in the desired diagnosis time T corresponding to the immediately succeeding trigger signal.

With the processing in step S21 to step S25, even if a heartbeat cycle/heartbeat period is disturbed, the apparatus deletes the sub-volume data acquired in the heartbeat disturbance time from the memory 18, and executes combining processing and display from the sub-volume data acquired immediately after the end of the heartbeat disturbance time.

Note that it is possible to apply the "first correction mode" described above to even a case in which the desired diagnosis time T is shorter than time t0+time t1 as in the case of the sub-volume B shown in FIG. 14. When applying the "first correction mode" to such a case, the apparatus determines the scan count in the desired diagnosis time T corresponding to $R_n$ at time $R_n$+d. If the scan count is less than a predetermined scan count, the apparatus deletes the sub-volume data acquired in the desired diagnosis time T from the memory 18, and executes scan processing again for the same sub-volume. As in the case shown in FIG. 11, this can obtain the special effect of allowing the user to recognize the occurrence of a disturbance of a heartbeat cycle/heartbeat period of the object in real time and visually recognize a full volume image suitable for diagnosis immediately after the recognition.

Furthermore, even in such a case, the apparatus may determine the elapse of a scan time corresponding to a reference scan count instead of determining a scan count. In this case, the apparatus may determine whether the interval between R waves (R-R interval) is equal to or more than time t0+time t1 (whether the current state is a so-called "Early Trigger" state).

<<Third Correction Mode>>

Figure 15:
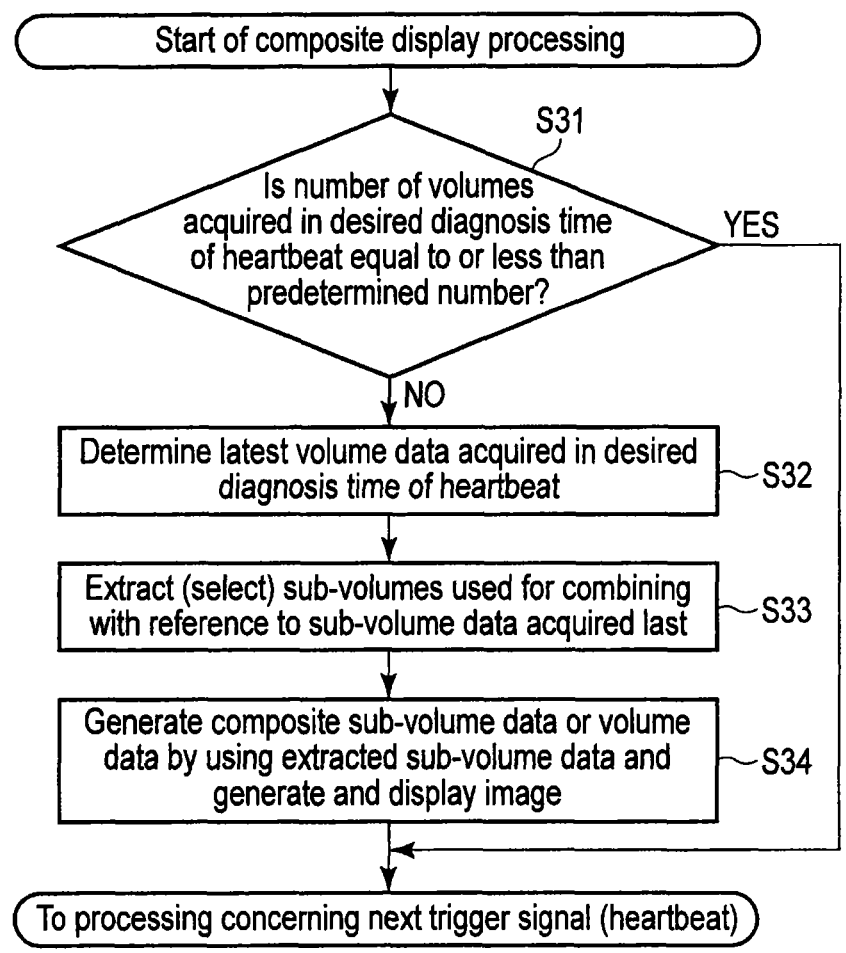
FIG. 15 is a flowchart associated with three-dimensional image combining processing in a "third correction mode".
Figure 16:
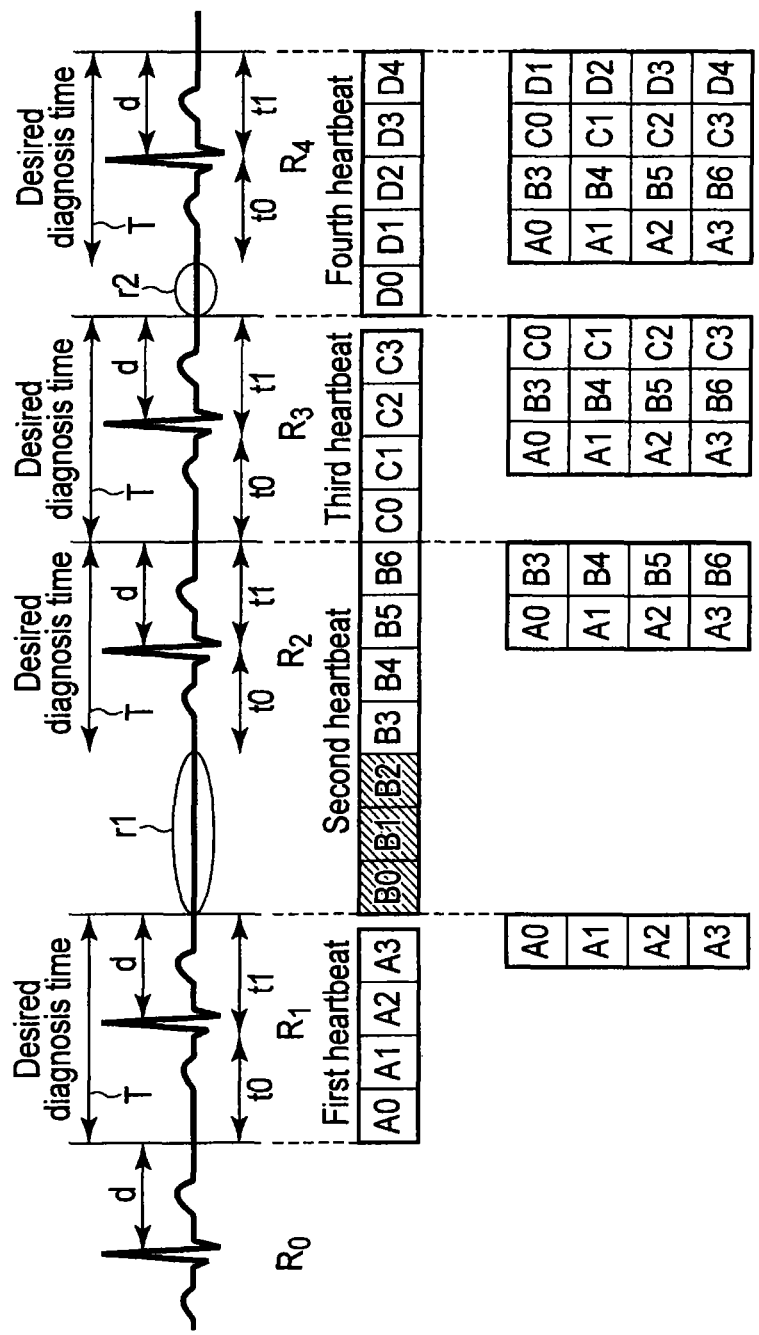
FIG. 16 is a sequence chart showing scan processing and three-dimensional image combining processing in the "third correction mode".

FIG. 15 is a flowchart according to three-dimensional image combining processing in a "third correction mode". FIG. 16 is a sequence chart showing scan processing and three-dimensional image combining processing in the "third correction mode". Note that scan processing in the third correction mode is substantially the same as the first embodiment shown in FIG. 9. In addition, the number of sub-volumes constituting a full volume and the desired diagnosis time T in which scan processing is executed are substantially the same as in the first correction mode.

As shown in FIG. 15, when starting composite display processing using the third correction mode, first of all, the system control unit 12 determines whether the number of volumes acquired in the desired heartbeat diagnosis time is equal to or less than a predetermined number (i.e., a number N of sub-volumes constituting a full volume (N=4 in this case)) (step S31). Upon determining that the number of volumes is equal to or less than N−1, the process shifts to combining processing at the next heartbeat without executing combining processing using the sub-volumes acquired at the heartbeat. Upon determining that the number of volumes is equal to or more than N, the process shifts to step S32 to execute combining processing using the sub-volumes acquired at the heartbeat.

The system control unit 12 determines the latest sub-volume data acquired in the desired heartbeat diagnosis time (step S32), and extracts sub-volume data used for combining processing with reference to the latest sub-volume data acquired (step S33). For example, in the second heartbeat shown in FIG. 16, upon completing the acquisition of sub-volume data in a desired diagnosis time, the system control unit 12 determines the sub-volume data B6 acquired last in the desired diagnosis time in the second heartbeat. The system control unit 12 then extracts the plurality of sub-volumes B3, B4, B5, and B6 corresponding to the respective time phases in a desired diagnosis time retroactively from the sub-volume data B6.

The system control unit 12 then generates composite sub-volume data constituted by the sub-volumes A0 to A3 and B3 to B6 by using the extracted sub-volumes, and generates and displays an ultrasonic image based on the composite sub-volume data (step 34).

At each subsequent heartbeat, the apparatus repeatedly executes the processing in steps S31 to S34. As a result, in the case shown in FIG. 16, the apparatus displays the image based on composite sub-volume data in the same time phases in real time in the first to third heartbeats, and generates and displays the ultrasonic image based on the full volume data.

Programming the series of processing performed by the ultrasonic diagnostic apparatus according to the above embodiment or storing the resultant program in a storage medium will facilitate sale and distribution of the series of processing as a software product independent of the ultrasonic diagnostic apparatus. It is also possible to use the technique according to the embodiment on other hardware (e.g., an ultrasonic image processing apparatus).

The above embodiment is not limited to application to an ultrasonic diagnostic apparatus. That is, the embodiment can be applied to a medical image diagnostic apparatus (e.g., an X-ray computed tomography, magnetic resonance imaging apparatus, X-ray diagnostic apparatus, and nuclear medicine diagnostic apparatus) which acquires and generates temporal volume data concerning the cyclically moving organ such as the heart. The embodiment can also be applied to general image diagnosis in which two-dimensional data, Doppler data, or the like, instead of volume data, is posteriorly rearranged by ECG gating.

As has been described above, this embodiment can provide an ultrasonic diagnostic apparatus, ultrasonic image processing apparatus, ultrasonic image acquisition program, and medical image diagnostic apparatus which can present a real-time three-dimensional area moving image obtained by combining data in the same time phases for the respective sub-volumes even when, for example, an object is an arrhythmic patient and a heartbeat cycle or heartbeat period is disturbed.

More specifically, the first correction mode can provide the special effect of allowing, even if a heartbeat cycle/heartbeat period is disturbed in an object, the user to recognize the occurrence of the disturbance of the heartbeat cycle/heartbeat period of the object (the occurrence of abnormality in the heart of the object) in real time and visually recognize a full volume image (in which adjacent sub-volume data coincide in phase) suitable for diagnosis immediately after the recognition.

According to the second correction mode, even if a heartbeat cycle/heartbeat period is disturbed, the apparatus automatically deletes the sub-volume data acquired in the heartbeat disturbance time from the memory 18 and executes combining processing and display from the sub-volume data acquired immediately after the end of the heartbeat disturbance time. This allows the user to visually recognize only a full volume image without any sense of strangeness (more suitable for diagnosis) as if there were no heartbeat cycle/heartbeat period disturbance.

According to the third correction mode, even if a heartbeat cycle/heartbeat period of an object is disturbed, having acquired a predetermined number or more of sub-volume data in a desired diagnosis time makes it possible to extract sub-volume data corresponding to the respective desired cardiac time phases with reference to the latest sub-volume data acquired in the desired diagnosis time. It is therefore possible to provide an accurate three-dimensional image in real time with high stability.

That is, according to this embodiment, even if a heartbeat cycle becomes unstable, the apparatus performs display (correction display) of a "full volume image slightly delayed from real-time display but suitable for diagnosis" (the full volume image constituted by sub-volume images coinciding in phase) while performing "real-time display directly reflecting unstable heartbeats" if the user wishes.

In addition, the user can freely select a time zone in which he/she wants to perform diagnosis and perform display so as to avoid any phase shifts between the respective sub-volumes. This can further prevent a decrease in frame rate. Since the user can properly display full volume data in the time zone in which the user wants to perform diagnosis, this technique can be applied to diagnosis of a patient with unstable heartbeats such as an arrhythmic patient and is expected to improve the diagnostic performance.

Note that the apparatus may use a trigger signal with reference to a P wave or T wave instead of a trigger signal with reference to an R wave as in the first embodiment. When using a trigger signal with reference to a P wave, the apparatus may generate a trigger signal at the time elapsed from the detection time point of a P wave by a predetermined period of time. When using a trigger signal with reference to a T wave, the apparatus may generate a trigger signal at the detection time point of a T wave.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
   a heartbeat signal acquisition unit configured to acquire a heartbeat signal of an object to be examined;
   a data acquisition unit configured to sequentially execute ultrasonic scanning on a plurality of sub-volumes to acquire sub-volume data corresponding to a plurality of time phases concerning each of the sub-volumes and each of a plurality of heartbeats;
   a data acquisition control unit configured to control the data acquisition unit to switch the sub-volume as an ultrasonic scan target at a first predetermined time phase elapsed by a first predetermined period from a second predetermined time phase for the each heartbeat;
   a combining processing unit configured to generate composite sub-volume data or a full volume data constituted by a plurality of sub-volume data by combining the sub-volume data acquired in a plurality of acquisition periods defined by the two adjacent first predetermined time phases;
   a heartbeat variation detection unit configured to detect at least one of a cyclic change of a heartbeat signal of the object and a change in the number of sub-volume data acquired in a detection period from the first predetermined time phase to a predetermined detection time phase; and
   a combining processing control unit configured to control the combining processing unit to extract a plurality of sub-volume data acquired in a predetermined diagnosis period from a plurality of sub-volume data acquired in each of the acquisition periods, the predetermined diagnosis period being a period from a fourth predetermined time phase to a fifth predetermined time phase, the fourth predetermined time phase being a phase retroactively from the second predetermined time phase by a second predetermined period and the fifth predetermined time phase being a phase elapsed by a third predetermined period from the second predetermined time phase, and to combine the extracted sub-volume data based on a detection result obtained by the heartbeat variation detection unit to generate the full volume data.

2. The ultrasonic diagnostic apparatus of claim 1, wherein the data acquisition unit repeatedly acquires the sub-volume data in the acquisition periods concerning each of the sub-volumes,
   the heartbeat variation detection unit performs the detection at an end time of each of the diagnosis periods as the detection time phase, and
   the combining processing control unit controls the combining processing unit to extract a predetermined number of sub-volumes retroactively with reference to latest sub-volume data acquired in each of the diagnosis period, and execute the combining processing again in the heartbeat by using the extracted sub-volume data if the heartbeat variation detection unit detects a heartbeat in which a cycle of a heartbeat signal of the object is longer than a predetermined cycle or the number of the sub-volume data acquired between the first predetermined time phase and the end time of each of the diagnosis periods is larger than a predetermined number.

3. The ultrasonic diagnostic apparatus of claim 1, wherein the data acquisition unit repeatedly acquires the sub-volume data in the acquisition periods concerning each of the sub-volumes,
   the heartbeat variation detection unit performs the detection in the second predetermined time phase as the detection time phase, and
   the combining processing control unit controls the combining processing unit to, if the heartbeat variation detection unit detects that a cycle of a heartbeat signal of the object is longer than a predetermined cycle or the number of the sub-volume data acquired between the first predetermined time phase and the second predetermined time phase is larger than a predetermined number, extract the predetermined number of sub-volumes retroactively with reference to latest sub-volume data acquired in each of the diagnosis period, and use the extracted sub-volume data for the combining processing.

4. The ultrasonic diagnostic apparatus of claim 1, wherein the data acquisition unit repeatedly acquires the sub-volume data in the acquisition periods concerning each of the sub-volumes, the heartbeat variation detection unit performs the detection at an end time of each of the diagnosis periods as the detection time phase, and the combining processing control unit controls the combining processing unit to extract a predetermined number of sub-volumes retroactively with reference to latest sub-volume data acquired in the diagnosis period and use the extracted sub-volume data for the combining processing.

5. The ultrasonic diagnostic apparatus of claim 1, further comprising a display unit configured to display the composite sub-volume data or the full volume data in real time.

6. The ultrasonic diagnostic apparatus of claim 1, wherein the second predetermined time phase is one of an R wave, a P wave, and an S wave.

7. A medical image diagnostic apparatus comprising:
a heartbeat signal acquisition unit configured to acquire a heartbeat signal of an object to be examined;
a data acquisition unit configured to sequentially execute imaging concerning a plurality of sub-volumes to acquire sub-volume data corresponding to a plurality of time phases concerning each of the sub-volumes and each of a plurality of heartbeats;
a data acquisition control unit configured to control the data acquisition unit to switch the sub-volume as an ultrasonic scan target at a first predetermined time phase elapsed by a first predetermined period from a second predetermined time phase for the each heartbeat;
a combining processing unit configured to generate composite sub-volume data or a full volume data constituted by a plurality of sub-volume data by combining the sub-volume data acquired in a plurality of acquisition periods defined by the two adjacent first predetermined time phases;
a heartbeat variation detection unit configured to detect at least one of a cyclic change of a heartbeat signal of the object and a change in the number of sub-volume data acquired in a detection period from the first predetermined time phase to a predetermined detection time phase; and
a combining processing control unit configured to control the combining processing unit to extract a plurality of sub-volume data acquired in a predetermined diagnosis period from a plurality of sub-volume data acquired in each of the acquisition periods, the predetermined diagnosis period being a period from a fourth predetermined time phase to a fifth predetermined time phase, the fourth predetermined time phase being a phase retroactively from the second predetermined time phase by a second predetermined period and the fifth predetermined time phase being a phase elapsed by a third predetermined period from the second predetermined time phase, and to combine the extracted sub-volume data based on a detection result obtained by the heartbeat variation detection unit to generate the frill volume data.

8. The medical image diagnostic apparatus of claim 7, wherein the data acquisition unit repeatedly acquires the sub-volume data in the acquisition periods concerning each of the sub-volumes, the heartbeat variation detection unit performs the detection at an end time of each of the diagnosis periods as the detection time phase, and the combining processing control unit controls the combining processing unit to extract a predetermined number of sub-volumes retroactively with reference to latest sub-volume data acquired in each of the diagnosis period, and execute the combining processing again in the heartbeat by using the extracted sub-volume data if the heartbeat variation detection unit detects a heartbeat in which a cycle of a heartbeat signal of the object is longer than a predetermined cycle or the number of the sub-volume data acquired between the first predetermined time phase and the end time of each of the diagnosis periods is larger than a predetermined number.

9. The medical image diagnostic apparatus of claim 7, wherein the data acquisition unit repeatedly acquires the sub-volume data in the acquisition periods concerning each of the sub-volumes, the heartbeat variation detection unit performs the detection in the second predetermined time phase as the detection time phase, and the combining processing control unit controls the combining processing unit to, if the heartbeat variation detection unit detects that a cycle of a heartbeat signal of the object is longer than a predetermined cycle or the number of the sub-volume data acquired between the first predetermined time phase and the second predetermined time phase is larger than a predetermined number, extract the predetermined number of sub-volumes retroactively with reference to latest sub-volume data acquired in each of the diagnosis period, and use the extracted sub-volume data for the combining processing.

10. The medical image diagnostic apparatus of claim 7, wherein the data acquisition unit repeatedly acquires the sub-volume data in the acquisition periods concerning each of the sub-volumes, the heartbeat variation detection unit performs the detection at an end time of each of the diagnosis periods as the detection time phase, and the combining processing control unit controls the combining processing unit to extract a predetermined number of sub-volumes retroactively with reference to latest sub-volume data acquired in the diagnosis period and use the extracted sub-volume data for the combining processing.

11. The medical image diagnostic apparatus of claim 7, further comprising a display unit configured to display the composite sub-volume data or the full volume data in real time.

12. The medical image diagnostic apparatus of claim 7, wherein the second predetermined time phase is one of an R wave, a P wave, and an S wave.

13. An ultrasonic image processing apparatus comprising:
a heartbeat signal storage unit configured to store a heartbeat signal of an object to be examined;

a data storage unit configured to store sub-volume data corresponding to a plurality of time phases concerning each of the sub-volumes, which are obtained by sequentially executing ultrasonic scanning on a plurality of sub-volumes in correspondence with time phases in a heartbeat;

a data acquisition control unit configured to control the data acquisition unit to switch the sub-volume as an ultrasonic scan target at a first predetermined time phase elapsed by a first predetermined period from a second predetermined time phase for the each heartbeat;

a combining processing unit configured to generate composite sub-volume data or a full volume data constituted by a plurality of sub-volume data by combining the sub-volume data acquired in a plurality of acquisition periods defined by the two adjacent first predetermined time phases;

a heartbeat variation detection unit configured to detect at least one of a cyclic change of a heartbeat signal of the object and a change in the number of sub-volume data acquired in a detection period from the first predetermined time phase to a predetermined detection time phase; and a combining processing control unit configured to control the combining processing unit to extract a plurality of sub-volume data acquired in a predetermined diagnosis period from a plurality of sub-volume data acquired in each of the acquisition periods, the predetermined diagnosis period being a period from a fourth predetermined time phase to a fifth predetermined time phase, the fourth predetermined time phase being a phase retroactively from the second predetermined time phase by a second predetermined period and the fifth predetermined time phase being a phase elapsed by a third predetermined period from the second predetermined time phase, and to combine the extracted sub-volume data based on a detection result obtained by the heartbeat variation detection unit to generate the full volume data.

* * * * *